United States Patent [19]
Awaya et al.

[11] Patent Number: 5,976,523
[45] Date of Patent: *Nov. 2, 1999

[54] METHOD FOR HEALING COMPROMISED TISSUES USING PYRIMIDINE DERIVATIVES

[75] Inventors: Akira Awaya, Yokohama; Fumiaki Ito, Ikoma; Kojun Torigoe, Fukui-ken; Ikuo Tomino, Yamaguchi-ken, all of Japan

[73] Assignee: Mitsui Pharmaceuticals, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/656,158

[22] Filed: May 16, 1996

[30] Foreign Application Priority Data

May 16, 1995 [JP] Japan ................................. 7-141074
Mar. 2, 1996 [JP] Japan ................................. 8-071329

[51] Int. Cl.[6] ........................................... A61K 38/00
[52] U.S. Cl. .................. 424/85.1; 514/255; 514/258; 514/234.2; 514/228.5; 530/300; 530/350
[58] Field of Search ................... 530/300, 350; 514/255, 258, 234.2, 228.5; 424/85.1

[56] References Cited

U.S. PATENT DOCUMENTS 4,959,368  9/1990  Awaya et al. .
5,304,555  4/1994  Awaya et al. .
5,376,636  12/1994  Rutherford et al. .

FOREIGN PATENT DOCUMENTS 0 454 026 A1  10/1991  European Pat. Off. .
WO 93/08828  5/1993  WIPO .

OTHER PUBLICATIONS

Dijke, "Growth Factors for Wound Healing" Biothelnology., v.7, pp. 793–798, 1989.
Awaya, "Neurotropic Pyrimidine Heterocyclic Compounds" Biol. Pharm. Bull. v. 16, No. 3, pp. 248–253, 1993.
Yasuhara, "Neurotropic Compound MS–818 promotes Angiogenesis induced by bFGF." Int. J. Clin. Pharm. Res., v. 15, No. (5/6) pp. 167–174, 1995.
Burgess, Embase ABS #89173023 (1989).
Barnes, Biosis ABS #89: 113709, 1988.
Fujitsuka et al., "Muscle Regeneration after Surgical Intervention and Acceleratory Healing by MS–818." Neuroscience Research Supplement 0 (18), 1993.
Int. J. Clin. Pharm. Res. XV (5/6) 167–174 (1995), The Neurotrophic Pyrimidine Heterocyclic Compound MS–818 Promotes the Angiogenesis Induced by Basic FGF, S. Yasuhara, et al.

*Primary Examiner*—Johann Richter
*Assistant Examiner*—Patrick R. Delaney
*Attorney, Agent, or Firm*—Knobbe, Martens, Olson & Bear, LLP

[57] ABSTRACT

The present invention provides a method for the screening of a wound-healing agent, which comprises determining a substance to be active as a wound-healing agent on the basis of potentiation or modification of biological activities of a growth and/or differentiation factor, a growth hormone or a cytokine. This invention also provides a wound-healing method, which comprises as an active ingredient a compound of the following formula (1) or formula (2) found to be active by the screening method.

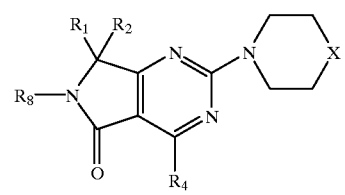

(1)

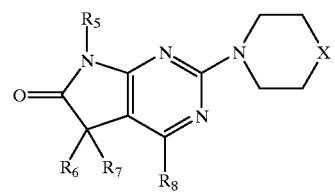

(2)

15 Claims, No Drawings

METHOD FOR HEALING COMPROMISED TISSUES USING PYRIMIDINE DERIVATIVES

BACKGROUND OF THE INVENTION a) Field of the Invention

This invention relates to the provision of a novel wound-healing agent and a novel method for the screening and provision of the wound-healing agent. More specifically, this invention is concerned with a novel medicament for the healing of wounds, for example, wounds by injuries such as simple incised wounds or cuts; wounds by various accidents or disasters; burns; scalds; bone fractures; tooth extraction wounds; operative wounds caused at affected sites or peripheries thereof during surgical operations such as in cornea vessels and various organs; body epithelial or endothelial ulcers; wounds such as keloids; texture injuries of gastrointestinal mucosae, e.g., gastric mucosa injuries, gastrointestinal ulcers, and mucosal injuries caused by inflammatory intestine diseases; hepatic injuries; bone damages; pseudoarthroses; necrosis of femoral head; ligamentous damages; periodontal damages; vascular damages; myocardial infarction; arterial seleroses; post-PTCA re-perfusion disorders; injuries by drugs or radiations, e.g., stomatitides and mucitis caused by chemotherapy or radiotherapy of cancers; decubiti by some causes such as bed-ridden health for a long period of time; and hemorrhoids. This invention also provides an original in vitro screening system and screening method for the provision of such wound-healing agents.

b) Description of the Related Art

To cure various wounds such as those described above, it is the current circumstance that with respect to injuries, injured parts are disinfected and then applied with a wound-covering material such as wet dressing or dry dressing or sutured with a surgical suture and patients then await until the injuries are healed by spontaneous ability of the their bodies. Recently, measures have been increasingly taken for the positive promotion of tissue repair or regeneration of such wounded parts, including use of "Aviten" (trade mark) or application of a material—which is formed of a matrix of a hyaluronic acid sponge and fragments of collagen or as a cell adhesion molecule, laminin or fibronectin coated on the matrix—to wounded parts.

It is stated that the process of healing of a wound is divided into an inflammation phase, a proliferation phase, granulation phase, and a remodeling phase, cicatrization (scar maturation) phase and proceeds through these phases or stages. In the granular tissue forming phase, formation of fibroblasts, myofibroblasts and new blood vessels is observed. In the cicatrization phase, parallel rearrangement of increased collagen on a skin surface and decrease and reconstruction of the new blood vessels are observed, whereby reorganization of the tissue is conducted. During these phases described above, various growth and/or differentiating factors and cytokines are considered to be produced by and released from various tissues containing fibroblasts, myofibroblasts or vascular endothelial cells, platelets, leukocytes, macrophages and the like and to give important action to the healing of the wound. Use of epidermal growth factors (EGFs) or basic fibroblast growth factors (bFGFs) has therefore started on a trial basis for the healing of apellous wounds or gastrointestinal ulcers (for example, Wolfe, M. M. et al., "Gastroenterology" 106, A212, 1994).

Further, external administration of bFGFs and the like are also being tested on animals with a view to promoting angiogenesis to perfuse cardiac muscle damaged by ischemia or the like.

As has been described above, it is performed actually or on a trial basis for the promotion of the process of healing of a wound to administer to the living body a growth and/or differentiation factor, a growth hormone, a cytokine or an adhesion molecule which takes part in the healing of a wound actually performed in the living body. It is the current situation that such substances are limited only to those derived from the living body.

When one wants to apply these substances, especially proteins for the healing of human wounds, a limitation is imposed on their administration route so that their effects are generally not expected to last over an extended period of time. For EGFs and bFGFs, local administration may be the best method for administration in many instances. Under the circumstances, however, local administration of ointments or the like may be performed first although whole body administration by injection or the like would also be attempted on a trial basis. Further, a growth and/or differentiation factor or a cytokine has a multipotent of functions so that it may exhibit not only wound-healing effects but also other undesired action. Its administration may therefore involve potential problems.

In addition, it is also necessary for the preparation of such a protein to process a human gene by genetic engineering to conduct its expression. Therefore, the protein becomes costly, and is also required to overcome various problems which are expected to arise upon its production as a pharmaceutical.

SUMMARY OF THE INVENTION

Not many wound-healing agents have been developed to date. The present inventors began to exercise their efforts with a view to finding novel wound-healing agents of excellent quality not only among proteins and peptides but also, especially among synthetic compounds. It may be contemplated to provide various in vivo experimental systems for the determination of wound-healing effects and to subject compounds, which may be considered as potential candidates of wound-healing agents, to screening one by one. This however requires lots of time and labor for the designing of these experimental systems and also substantial time and skill for the assay and evaluation. Accordingly this screening method cannot be practiced easily.

With the foregoing in view, the present inventors ingeniously came up with an idea, that is, to design an in vitro experimental system for the search of substances having wound-healing activities. Having been attracted to growth and/or differentiation factors, growth hormones and cytokines out of various substances which take part in the process of wound healing, the present inventors considered selecting substances which may act in association with these factors or act to assist them. Further, the present inventors also considered using, instead of a laborious in vivo experimental system, an in vivo experimental system which is close to an in vitro system and is simple and economical. As a result of an extensive investigation, it has been found that compounds—which were confirmed to potentiate or modify biological activities of growth and/or differentiation factors, growth hormones and cytokines by an in vitro experimental system or an economical in vivo experimental system close to an in vitro system—actually exhibit wound-healing effects through accelerations of the healing of wounds in apellous wound models, skin cut and suture models, artery island skin flap take rate test models, digestive tract ulcer models, hepatic injury model, intra-aortic balloon catheter paratripsis models, cornea injury models, bone fracture models, scald models, decubitus models and the like of rats, mice, rabbits and the like.

The present invention has been completed based on such findings. Specifically, the present invention is based on the finding that a substance—which can enpotentiate or modify in vitro or like biological activities of growth and/or differentiation factors, growth hormones or cytokines—has wound-healing effects. The present invention therefore provides a wound-healing method, which comprises administering to a patient a wound-healing agent comprising as an active ingredient a substance having an activity to potentiate or modify biological activities of a growth and/or differentiation factor, a growth hormone or a cytokine. The present invention also proposes and provides a novel method for the screening of a wound-healing agent, which comprises determining a substance to be effective as a wound-healing agent on the basis of potentiation or modification of biological activities of a growth and/or differentiation factor, a growth hormone or a cytokine.

By the present inventors, certain synthetic pyrimidine compounds were previously screened as substances capable of promoting neurite extension of neuroblastoma cells (Awaya, A., et al., "Biol. Pharm. Bull.", 16(3), 248–253, 1993) and were found to promote restoration or repair of nerves in an animal which had been subjected to neural injuries or neulogical disorders. The present inventors newly provide these synthetic pyrimidine compounds as such wound-healing agents.

DETAILED DESCRIPTION OF THE INVENTION AND PREFERRED EMBODIMENTS

Synthetic pyrimidine compounds which can be provided as wound-healing agents by the present invention include 2-substituted-6-alkyl-5-oxo-5,6-dihydro(7H)-pyrro[3,4-d] pyrimidine compounds, 2-substituted-7-alkyl-6-oxo-5,6-dihydro(7H)pyrro[2,3-d]pyrimidine compounds and salts thereof, which are disclosed inter alia in WO No. 87/04928, U.S. Pat. No. 4,959,368, Japanese Patent Application Laid-Open (Kokai) No. 139,572/1989, U.S. Pat. No. 5,304,555, Japanese Patent Application Laid-Open (Kokai) No. 40,483/1989, Japanese Patent Application Laid-Open (Kokai) No. 221,275/1990 and Japanese Patent Publication (Kokoku) No. 5,887/1996. More specifically, they can be compounds represented by the following formula (1) or formula (2):

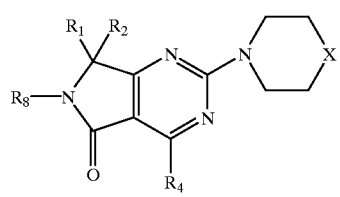

(1)

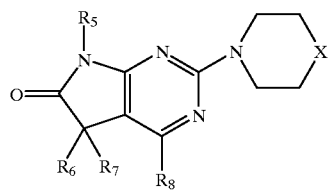

(2)

wherein $R_1$ to $R_8$ independently represent a hydrogen atom, a lower alkyl (especially $C_1$–$C_7$ alkyl) group, $CH_3OCH_2CH_2$—, —$CH_2CONH_2$, —$COCH_3$, —$COC_2H_5$ or -$CH_2OCOC_2H_5$, and X represents >NH, >N—$CH_3$, >N—$C_2H_5$, >N-ph, >N—$CH_2$-ph, >N—CH-$ph_2$, >N—$COCH_3$, >N—$COOC_2H_5$, >N—$SO_2CH_3$, >$CH_2$, >$CHCH_3$, >$CHC_2H_5$, -O- or -S- in which ph stands for a phenyl group.

Typical illustrative compounds of formula (1) include:

2-Piperazino-6-methyl-5-oxo-5,6-dihydro(7H)pyrro-[3,4-d]pyrimidine, 2-(4-Methylpiperazino-6-methyl-5-oxo-5,6-dihydro-(7H) pyrro[3,4 -d]pyrimidine, 2-(4-Ethylpiperazino-6-methyl-5-oxo-5,6-dihydro-(7H) pyrro[3,4-d]pyrimidine, 2-Piperidino-6-methyl-5-oxo-5,6-dihydro(7H)pyrro-[3,4-d]pyrimidine, 2-(4-Methylpiperidino)-6-methyl-5-oxo-5,6-dihydro(7H) pyrro[3,4-d]pyrimidine, 2-(4-Ethylpiperidino)-6-methyl-5-oxo-5,6-dihydro-(7H) pyrro[3,4-d]pyrimidine, 2-Morpholino-6-methyl-5-oxo-5,6-dihydro(7H)pyrro-[3, 4-d]pyrimidine, 2-Thiomorpholino-6-methyl-5-oxo-5,6-dihydro(7H)-pyrro[3,4-d]pyrimidine, 2-Piperazino-6-ethyl-5-oxo-5,6-dihydro(7H)pyrro-[3,4-d]pyrimidine, 2-Piperazino-6-isopropyl-5-oxo-5,6-dihydro(7H)-pyrro [3,4-d]pyrimidine, 2-Piperazino-6-n-butyl-5-oxo-5,6-dihydro(7H)-pyrro[3, 4-d]pyrimidine, 2-Piperazino-6-sec.-butyl-5-oxo-5,6-dihydro(7H)-pyrro [3,4-d]pyrimidine, 2-Piperazino-6-t-butyl-5-oxo-5,6-dihydro(7H)-pyrro[3,4-d]pyrimidine, 2-Piperazino-4,6-dimethyl-5-oxo-5,6-dihydro(7H)-pyrro [3,4-d]pyrimidine, 2-Piperazino-6,7-dimethyl-5-oxo-5,6-dihydro(7H)-pyrro [3,4-d]pyrimidine, 2-Piperazino-6,7,7-trimethyl-5-oxo-5,6-dihydro-(7H) pyrro[3,4-d]pyrimidine, 2-Piperidino-4,6-dimethyl-5-oxo-5,6-dihydro(7H)-pyrro [3,4-d]pyrimidine, 2-Piperidino-6,7,7-trimethyl-5-oxo-5,6-dihydro-(7H) pyrro[3,4-d]pyrimidine, 2-Piperazino-7-methyl-6-ethyl-5-oxo-5,6-dihydro-(7H) pyrro[3,4-d]pyrimidine, and 2-Piperazino-4-methyl-6-ethyl-5-oxo-5,6-dihydro-(7H) pyrro[3,4-d]pyrimidine.

Typical illustrative compounds of formula (2) include:

2-Piperazino-7-methyl-6-oxo-5,6-dihydro(7H)pyrro-[2, 3-d]pyriinidine, 2-(4-Methylpiperazino)-7-methyl-6-oxo-5,6-dihydro(7H) pyrro[2,3-d]pyrimidine, 2-(4-Ethylpiperazino)-7-methyl-6-oxo-5,6-dihydro-(7H) pyrro[2,3-d]pyrimidine, 2-(4-N-Acetylpiperazino)-7-methyl-6-oxo-5,6-dihydro (7H)pyrro[2,3-d]pyrimidine, 2-Piperidino-7-methyl-6-oxo-5,6-dihydro(7H)pyrro-[2,3-d]pyrimidine, 2-(4-Methylpiperidino)-7-methyl-6-oxo-5,6-dihydro(7H) pyrro[2,3-d]pyrimidine, 4-(Ethylpiperidino)-7-methyl-6-oxo-5,6-dihydro-(7H) pyrro[2,3-d]pyrimidine, 2-Morpholino-7-methyl-6-oxo-5,6-dihydro(7H)pyrro-[2,3-d]pyrimidine, 2-Thiomorpholino-7-methyl-6-oxo-5,6-dihydro(7H)-pyrro[2,3-d]pyrimidine, 2-Piperidino-7-ethyl-6-oxo-5,6-dihydro(7H)pyrro-[2,3-d] pyrimidine, 2-Piperidino-7-n-propyl-6-oxo-5,6-dihydro(7H)-pyrro[2,3-d]pyrimidine, 2-Piperidino-7-isopropyl-6-oxo-5,6-dihydro(7H)-pyrro [2,3-d]pyrimidine, 2-Piperidino-7-n-butyl-6-oxo-5,6-dihydro(7H)-pyrro[2,3-d]pyrimidine, 2-Piperidino-7-t-butyl-6-oxo-5,6-dihydro(7H)-pyrro[2,3-d]pyrimidine, 2-Piperidino-5-methyl-6-oxo-5,6-dihydro(7H)pyrro-[2,3-d]pyrimidine, 2-Piperazino-5-methyl-6-oxo-5,6-dihydro(7H)pyrro-[2,3-d]pyrimidine, 2-Piperazino-4,7-dimethyl-6-oxo-5,6-dihydro(7H)-pyrro [2,3-d]pyrimidine, 2-Piperidino-5,7-dimethyl-6-oxo-5,6-dihydro(7H)-pyrro [2,3-d]pyrimidine, 2-Piperidino-5,5,7-trimethyl-6-oxo-5,6-dihydro-(7H) pyrro[2,3-d]pyrimidine, 2-Piperazino-5,7-dimethyl-6-oxo-5,6-dihydro(7H)-pyrro [2,3-d]pyrimidine, 2-Piperazino-5,5,7-trimethyl-6-oxo-5,6-dihydro-(7H) pyrro[2,3-d]pyrimidine, 2-Piperidino-4-methyl-7-ethyl-6-oxo-5,6-dihydro-(7H) pyrro[2,3-d]pyrimidine, and 2-Piperidino-5-methyl-7-ethyl-6-oxo-5,6-dihydro-(7H) pyrro[2,3-d]pyrimidine.

Healing of a wound is a process in which proliferation induction, migration, proliferation stop, differentiation and the like of cells take place under cooperative control. A variety of growth and/or differentiation factors, growth hormones or cytokines described above occur and play their own roles. Although finding of a wound-healing agent has heretofore been conducted by administering a test substance to a skin defect model of rats, mice, rabbits or the like and measuring its activity as described above, in vitro models which are simpler and less costly and typify a healing process of a wound have been devised. For example, there is a method in which human epidermic keratinocytes are cultured for about 1 week in contracted collagen gel containing fibroblasts to reconstitute a skin tissue, the skin tissue is centrally cut off in the form of a circle of 4 mm in diameter over the entire thickness thereof, and further the skin tissue is cultivated in separately-prepared collagen, and the cultivation is continued to observe the process of regeneration of a tissue.

It is stated that according to the above model, cells are allowed to migrate out from a free edge of a defect of the reconstituted skin toward a center of the wound and to cover up the defect in 1 week after the formation of the defect, that the cells proliferate, stratify and differentiate to recover the original tissue architecture resembling a normal skin and that the process of healing of the wound can be observed in a state close to an in vivo model although it is a culture system (Yasutoshi Suzuki, et al., "Paper No. 1202 of Proceedings of the Japanese Cancer Association Addressed at the 53rd Annual Meeting", 353, 1994. In the present invention, such an original model was simplified further and by choosing, as targets, only growth and/or differentiation factors, growth hormones and cytokines which play certain role in the healing of wounds, assays were conducted to determine whether the actions of such biologically-active substances are potentiated or modified with a test compound. These assays led to the finding of substances having such potentiating or modifying activities. As these substances have been found to promote healing by visual observation, measurement of skin tensile strengths or the like. The screening method of the present invention for wound-healing agents therefore has a useful value as a novel assay system which can reasonably meet requirements.

In an in vitro model making use of an EGF, epithelial cells are placed in an upper well of a Boyden's chamber whereas the EGF and a test compound are added to a lower well of the same chamber. By simply measuring the number of migrating cells, it is possible to determine whether the test compound has a potential as a wound-healing agent. As the epithelial cells, any cells can be used insofar as they are available as epitheliocytes. Illustrative examples include canine MTCK renal cells, TMK cells, and mucosal cells of various animals such as those of their esophagi, stomachs, small intestines, duodenums, large intestines, lungs, bronchi, livers, biliary tracts, kidneys, pancreas, spleens, thymus and the like.

Concerning an in vitro model making use of a bFGF, fibroblasts are placed in an upper well of a Boyden's chamber whereas the bFGG and a test compound are added to a lower well of the same chamber. By simply measuring the number of migrating cells or simply measuring cell-growth-promoting activity, it is also possible to determine whether the test compound has a potential as a wound-healing agent. Any fibroblasts are usable insofar as they are available. Illustrative examples include fibroblasts of tissues of the whole bodies of various animals such as Balb/3T3 cells, cultured vascular endothelial cells and myofibroblasts.

For a bFGF, various assay systems assessing the angiogenesis activity of the bFGF as an index are usable. The shells of chick embryos are fenestrated centrally corresponding to the air spaces thereof, whereby the chorioallantoic membranes (CAMS) are exposed. Solutions of the bFGF and a test medicament at various concentrations were applied onto the respective CAMs. Incubation was continued. Several days later, the degrees of angiogenesis were investigated under a microscope. This method is preferably employed. Each test medicament, which has been found to promote the angiogenesis activity of the bFGF in this experimental system, promotes vascularization in the corium when employed in combination upon grafting a cultured vascular endothelial cells sheet between an artificial skin and a grafted bed in a system in which the artificial skin is grafted subsequent to the formation of an appellous wound in the skin to a full thickness at a back region of a rat. The test medicament is therefore found to be useful for the reduction of a time required for the construction of a skin-equivalent tissue. Further, a compound which has been revealed to have activity to potentiate or modify the angiogenesis ability of a bFGF by the CAM method has demonstrated to promote healing in a skin cut and suture model of a mouse, rat, rabbit or the like, to increase the take rate of an artery island skin flap in an artery island skin flap take rate test model and also to promote restoration and regeneration in a rat aortic balloon catheter paratripsis model. Also with respect to a VEGF, its angiogenesis activity can be assayed in a similar system.

With respect to other FGFs, TGF-α, TGF-β, PDGFs, PD-ECGFs, BMPs, HGFs, midkines, TNFs, insulin, IGF-I, II, keratinocyte growth factors, ECGFs, fibroblast-derived epithelial cell growth factors, G-CSFs, M-CSFs, GM-CSFs, TPOs, LIFs, SCFs, EPOs, ADFS, MIP-α, transferrin, thrombin, thrombomodulin, IL-1, IL-4, IL-6, IL-8, HRFS, monocyte chemotaxis activators, CGRPs, SODs, angiotensins, prostaglandins, serotonin, collagen, fibronectin, laminin and the like and their homologues, it is possible to use assay systems similar to those employed for EGFs, aFGFs and bFGFs. Each test medicament as a wound-healing agent can be screened by culturing target cells, on which the above growth and/or differentiation factors, growth hormones and cytokines are known to act, in an assay equipment such as a Boyden's chamber and then assaying growth and/or differentiation of the cells, a release of a physiologically active substance from the cells, mobility of the cells such as their migrating, or a morphological change of the cells. As measurement parameters, morphological observation, gene and nucleic acid levels, synthesis levels of proteins, enzymatic activities and the like are investigated. Further, it is also possible to assay inherent biological activities of the individual growth and/or differentiation factors, growth hormones and cytokines in in vitro systems or in in vivo system close to such in vitro systems.

Substances which have been found by such assay systems, by themselves, do not have in vitro biological activities similar to those of growth and/or differentiation factors and cytokines or even if equipped with such biological activities, their biological activities are weak. However, in the living body having a wounded part, they potentiate or modify the biological activities of the growth and/or differentiation factors, growth hormones and cytokines at a site where these factors, hormones and cytokines are acting. In the process of healing of a wound, these substances potentiate or modify the activities of such factors, hormones and cytokines only when they are acting rather than working all the time. These substances are therefore considered to develop no side effect and also to have low mutagenicity. When these factors, hormones and cytokines continue to act and excessive reaction or phenomenon such as cicatrization or the like is expected to proceed, it is only necessary to stop the administration of the substances. It is desired to administer these substances either singly or in combination with recombinant proteins of these factors, hormones and cytokines to the living body at an appropriate time while these factors, hormones and cytokines are acting. It is also considered appropriate to administer these substances either singly or in combination with or as mixtures with these proteins so that in the process of healing of a wound, action of the growth and/or differentiation factors and the like is promptly developed for a short period of time in the living body without causing problems such as prolongation and intractability of the healing of the wound due to the action of these endogenous growth and/or differentiation factors over an extended period of time at the wounded site or the long-term administration of proteins of these factors from the outside.

In the process of restoration and healing of a gastrointestinal ulcer, the healing proceeds from granulation to epidermalization. Namely, in an initial stage of inflammation occurred immediately after loss of a mucosa, PDGF and TGF-β are released from platelets. These factors cause migration of macrophages. Such macrophages themselves release growth factors like PDGF and TGF-β, so that the healing process proceeds in an accelerated fashion. In 2 to 3 days, fibroblasts are allowed to grow by PDGF, FGF, EGF and the like. At the same time, ECM is accumulated by TGF-β and further, angiogenesis takes place under the action of FGF and the like. Granulation is therefore completed in this manner. Next, by HGF released from fibroblasts in granulations or by TFG-α or EFG, epithelial cells are caused to migrate and grow and cover the granulations. At substantially the same time, reform of connective tissue takes place [Akira Terano, et al., "Medical Practice—Saibo Zoshoku Inshi to Shokasei Kaiyo (Cell Growth Factors and Gastrointestinal Ulcers]", 10(4), 653–757, 1993.

The pyrimidine compounds according to the present invention effectively act on such wound-healing processes and have wound-healing activities.

The compounds of formula (1) or formula (2) according to this invention have been found to be useful as wound-healing medicaments.

The compounds of formula (1) or formula (2) are used normally in the form of pharmaceutical compositions, and administered through various routes, for example, oral, subcutaneous, intramuscular, intravenous, intranasal, skin permeation and intrarectal routes.

The present invention also includes a pharmaceutical composition comprising a pharmaceutically-acceptable carrier and a compound of formula (1) or formula (2) or its pharmaceutically-acceptable salt as an active ingredient.

Examples of the pharmaceutically-acceptable salt of the compound of formula (1) or formula (2) include salts formed from acids capable of forming pharmaceutically-acceptable non-toxic acid-addition salts containing anions, such as the hydrochloride, hydrobromide, sulfate, bisulfite, phosphate, acid phosphate, acetate, maleate, fumarate, succinate, lactate, tartrate, benzoate, citrate, gluconate, glucanate, methanesulfonate, p-toluenesulfonate and naphthalenesulfonate, and their hydrates, as well as the quaternary ammonium (or amine) salt and its hydrate.

The composition of this invention may be formulated into tablets, capsules, powders, granules, troches, cachet wafer capsules, elixirs, emulsions, solutions, syrups, suspensions, aerosols, ointments, sterilized injection solution, molded cataplasmas, soft and hard gelatin capsules, "alzet" (trade mark) pump capsules, pellets, suppositories, and aseptic packed powders.

Examples of the pharmaceutically-acceptable carrier (or diluent) include lactose, glucose, sucrose, sorbitol, mannitol, corn starch, crystalline cellulose, gum arabic, calcium phosphate, arginates, calcium silicate, microcrystalline cellulose, polyvinyl pyrrolidone, tragacanth gum, gelatin, syrup, methyl cellulose, carboxymethyl cellulose, methylhydroxybenzoic acid esters, propylhydroxybenzoic acid esters, talc, magnesium stearate, inert polymers, water, and mineral oils.

Both solid and liquid compositions may contain, in addition to such a carrier as exemplified above, one or more of fillers, binders, lubricants, wetting agents, disintegrants, emulsifying agents, suspending agents, preservatives, sweetening agents and flavoring agents. The composition of this invention may be formulated such that after administration to a patient, the active ingredient is released rapidly, continuously or slowly.

In the case of oral administration, the compound of formula (1) or formula (2) is mixed with a carrier or diluent and formed into tablets, capsules or the like. In the case of parenteral administration, the active ingredient is dissolved in a 10% aqueous solution of glucose, isotonic salt water, sterilized water or a like liquid, and hermetically filled in vials or ampoules for intravenous instillation or injection or intramuscular injection. Advantageously, a dissolution aid, a local anesthetic agent, a preservative and a buffer may also be included into the medium. To increase stability, it is possible to lyophilize the present composition after introduction into a vial or ampoule. Other examples of preparations for parenteral administration include those administered percutaneously, such as ointments and cataplasms. In this case a molded cataplasm or a tape is advantageous. Further examples include pellets for direct implantation in specific dyscratic parts, tissues or bones and "alzet" (trade name) pump capsules. Illustrative resins usable for the preparation of such pellets include poly(2-hydroxyethylmethacrylate) ad ethylene-vinyl acetate copolymer.

The composition of this invention contains generally 0.1 to 2,000 mg, preferably 0.5 to 1,000 mg of the active ingredient per unit dosage form.

The compound of formula (1) or formula (2) is effective over a wide dosage range. For example, the amount of the compound administered per day usually falls within a range of 0.03 mg/kg to 100 mg/kg. The amount of the compound to be actually administered is determined by a physician depending, for example, upon the type of the compound administered, and the age, body weight, reaction, condition, etc. of the patient and the administration route. The above dosage range, therefore, does not limit the scope of the invention. The suitable number of administrations is usually 1 to 6, preferably 1 to 4, daily.

The compound of formula (1) or formula (2) by itself is an effective wound-healing medicament. If required, it may be administered in combination with one or more other equally effective drugs. Examples of such additional drugs include such various growth and/or differentiation factors, growth hormones, cytokines, and zinc.

Preparation examples of the compound of formula (1) or (2) useful as a healing agent in the present invention have already been reported by the present inventors in patent applications and articles to which reference may be had [WO No. 87/04928, U.S. Pat. No. 4,959,368, Japanese Patent Application Laid-Open (Kokai) No. 139,572/1989, U.S. Pat. No. 5,304,555, Japanese Patent Application Laid-Open (Kokai) No. 40,483/1989, Japanese Patent Application Laid-Open (Kokai) No. 221,275/1990, Japanese Patent Publication (Kokoku) No. 5,887/1996, and Biol. Pharm. Bull., 16(3), 248–253, 1993].

The present invention will hereinafter be described in further detail by the following Examples and Experiments. It is however to be borne in mind that the present invention is not limited to them.

EXAMPLE 1

Tablets each containing 10 mg of an active ingredient were prepared by the following procedures.

|  | Per tablet |
| --- | --- |
| Active ingredient | 10 mg |
| Corn starch | 55 mg |
| Crystalline cellulose | 35 mg |
| Polyvinyl pyrrolidione (as 10% aq. soln.) | 5 mg |
| Carboxymethyl cellulose calcium | 10 mg |
| Nagnesium stearate | 4 mg |
| Talc | 1 mg |
| Total | 120 mg |

The active ingredient, corn starch and crystalline cellulose were passed through an 80-mesh sieve for thorough mixing. The mixed powder was granulated together with the polyvinyl pyrrolidone solution, and passed through an 18-mesh sieve. The resulting granules were dried at 50 to 60° C. and again passed through an 18-mesh sieve t adjust their sizes. The carboxymethyl cellulose calcium, magnesium stearate and talc, which had been passed in advance through an 80-mesh sieve, were added to the granules. They were mixed and tableted by a tableting machine to produce tablets each having a weight of 120 mg.

EXAMPLE 2

Tablets each containing 200 mg of an active ingredient were produced by the following procedures.

|  | Per tablet |
| --- | --- |
| Active ingredient | 200 mg |
| Corn starch | 50 mg |
| Crystalline cellulose | 42 mg |
| Light silicic anhydride | 7 mg |
| Magnesium stearate | 1 mg |
| Total | 300 mg |

The above components were passed through an 80-mesh sieve for thorough mixing. The resulting mixed powder was compression-molded to produce tablets each having a weight of 300 mg.

EXAMPLE 3

Capsules each containing 100 mg of an active ingredient were produced by the following procedures.

|  | Per capsule |
| --- | --- |
| Active ingredient | 100 mg |
| Corn starch | 40 mg |
| Lactose | 5 mg |
| Magnesium stearate | 5 mg |
| Total | 150 mg |

The above components were mixed, and passed through an 80-mesh sieve for thorough mixing. The resulting mixed powder was filled into capsules in an amount of 150 mg for each.

EXAMPLE 4

An injectable preparation in vials each containing 5 mg of an active ingredient were produced by the following procedures for dissolution just before use.

|  | Per vial |
|---|---|
| Active ingredient | 5 mg |
| Mannitol | 50 mg |
| Total | 55 mg |

Just prior to use, the preparation was dissolved in 1 ml of distilled water for injection, and administered.

EXAMPLE 5

An injectable preparation in ampoules each containing 50 mg of an active ingredient was produced in accordance with the following recipe.

|  | Per ampoule |
|---|---|
| Active ingredient | 50 mg |
| Sodium chloride | 18 mg |
| Distilled water for injection | q.s. |
| Total | 2 ml |

EXAMPLE 6

An adhesive patch containing 17.5 mg of an active ingredient was produced by the following procedures.

Ten parts of poly(ammonium acrylate) were dissolved in 60 parts of water. Two parts of glycerin diglycidyl ether were dissolved under heat in 10 parts of water. Furthermore, 10 parts of polyethylene glycol (grade: 400), 10 parts of water and 1 part of an active ingredient were stirred into a solution. While an aqueous solution of poly(ammonium acrylate) was stirred, an aqueous solution of glycerin diglycidyl ether and an aqueous solution of the active ingredient in polyethylene glycol and water were added and mixed. The resulting solution for a medicament-containing hydrogel was coated on a pliable plastic film so that the rate of the active ingredient was 0.5 mg per $cm^2$. The surface was covered with releasing paper and cut into a size of 35 $cm^2$ to form an adhesive patch.

EXAMPLE 7

An adhesive patch containing 10 mg of an active ingredient was produced by the following procedures.

An aqueous sol was prepared from 100 parts of poly(sodium acrylate), 100 parts of glycerin, 150 parts of water, 0.2 part of triepoxypropyl isocyanurate, 100 parts of ethanol, 25 parts of isopropyl myristate, 25 parts of propylene glycol and 15 parts of the active ingredient. The sol was then coated to a thickness of 100 $\mu m$ on a non-woven fabric surface of a composite film composed of rayon non-woven fabric and a polyethylene film to form an adhesive layer containing the medicament. The amount of the release aids (isopropyl myristate and propylene glycol) contained in this layer was about 20% by weight. The adhesive layer was then crosslinked at 25° C. for 24 hours, and a releasing film was bonded to the adhesive layer surface. The entire film was then cut into pieces each having an area of 35 $cm^2$.

EXAMPLE 8

The procedures of Example 4 were followed except for the additional inclusion of EGF in an amount of 1 mg per vial.

EXAMPLE 9

The procedures of Example 4 were followed except for the additional inclusion of bFGF in an amount of 1 mg per vial.

EXAMPLE 10

The procedures of Example 5 were followed except for the additional inclusion of EGF in an amount of 1 mg per ampoule.

EXAMPLE 11

The procedures of Example 5 were followed except for the additional inclusion of bFGF in an amount of 1 mg per ampoule.

EXAMPLE 12

The procedures of Example 6 were followed except for the additional inclusion of EGF in an amount of 0.2 mg per unit preparation.

EXAMPLE 13

The procedures of Example 6 were followed except for the additional inclusion of bFGF in an amount of 0.2 mg per unit preparation.

EXAMPLE 14

The procedures of Example 7 were followed except for the additional inclusion of EGF in an amount of 0.2 mg per unit preparation.

EXAMPLE 15

The procedures of Example 7 were followed except for the additional inclusion of bFGF in an amount of 0.2 mg per unit preparation.

EXAMPLE 16

Coarse sand-like crystals of poly(2-hydroxyethyl methacrylate) (product of Polysciences, Inc.) were placed in a mortar and in a clean bench, were aseptically ground into fine-particulate powder by a pestle. Ten milligrams of the powder were taken in a sterilized Petri dish, followed by the addition of 10 $\mu l$ of 99% ethyl alcohol and 10 $\mu l$ of an aqueous solution containing 0.5 mg of an active ingredient. The resulting mixture was thoroughly stirred into a pasty mass and was then dried.

EXAMPLE 17

The procedures of Example 16 were followed except for the additional inclusion of EGF in an amount of 0.5 $\mu g$ per unit preparation.

EXAMPLE 18

The procedures of Example 16 were followed except for the additional inclusion of bFGF in an amount of 0.5 $\mu g$ per unit preparation.

EXAMPLE 19

The procedures of Example 16 were followed except for the additional inclusion of Midkine in an amount of 0.5 $\mu g$ per unit preparation.

EXAMPLE 20

The procedures of Example 16 were followed except for the additional inclusion of PDGF in an amount of 0.5 $\mu g$ per unit preparation.

EXAMPLE 21

The procedures of Example 16 were followed except for the additional inclusion of TGF in an amount of 0.5 $\mu g$ per unit preparation.

EXAMPLE 22

The procedures of Example 16 were followed except for the additional inclusion of IGF in an amount of 0.5 μg per unit preparation.

EXAMPLE 23

The procedures of Example 16 were followed except for the additional inclusion of IL-4 in an amount of 0.5 μg per unit preparation.

EXAMPLE 24

TMK1 cells, low-differentiating epithelial cells, were treated with trypsin. The cells were washed with RPMI 1640 culture medium containing 0.25% BSA and were then resuspended in the same culture medium. After a culture medium containing a solution or mixed solution of one or more of growth and/or differentiation factors, growth hormones and cytokines—such as EGF, bFGF, HGF, TGF-β, PDGF, IGF-1, transferrin and CGRP—and/or a pyrimidine compound according to the present invention was added beforehand in an amount of 200 μl in a lower well of a Boyden's chamber, a filter coated with type IV collagen was placed and 200 μl of the above suspension containing $1\times10^6$ cells/ml of the TMK1 cells were then added to an upper well, followed by incubation for 4 hours. The culture medium in the lower well was then subjected to fixing and staining, and cells which had migrated therein were counted. Experiments were conducted concurrently in three chambers. In each experiment, the culture medium was observed in five (5) visual fields under a microscope and cells in each visual field were counted.

The values obtained from the above counting will be given below. Each value will be presented as a mean ±S.D. and with respect to each compound, numbers of cells will be presented in the order of a) control, b) each pyrimidine compound (whose concentration will be specifically indicated), c) 10 ng/ml of EGF, and d) a mixed solution of each pyrimidine compound + EGF.

With respect to 2-piperazino-6-methyl-5-oxo-5,6-dihydro (7H)pyrro[3,4-d]pyrimidine maleate, the numbers of cells counted were: a) 5.7±0.5, b) 7.4±3.0 (1 mM), c) 80±8.0, and d) 111.2±8.0.

Concerning 2-piperidino-7-methyl-6-oxo-5,6-dihydro (7H)pyrro[3,4-d]pyrimidine maleate, the numbers of cells counted were: a) 1.6±0.7, b) 2.9±1.0 (0.1 mM), c) 17.5±1.6, and d) 20.9±3.9.

As to 2-(4-ethylpiperidino)-7-methyl-6-oxo-5,6-dihydro (7H)pyrro[2,3-d]pyrimidine maleate, the numbers of cells counted were: a) 9.1±1.0, b) 28.6±18.4 (0.1 mM), c) 93.2±2.0, and d) 144±3.1.

In regard to 2-piperidino-5,5,7-trimethyl-6-oxo-5,6-dihydro(7H)pyrro[3,4-d]pyrimidine maleate, the numbers of cells counted were: a) 24±12.5, b) 33±12.6 (0.1 mM), c) 130.9±15.9, and d) 147.2±13.2.

As is appreciated from the above values, the pyrimidine compounds have each been found to synergistically potentiate the action of EGF. These compounds were also found to have in vivo wound-healing effects as demonstrated inter alia by promoted smooth healing of skin wounds at cut and sutured skin sites of mice, rats, rabbits and the like. This finding was in conformity with the in vitro finding. This experimental method has therefore been recognized to be excellent as a screening method for wound-healing agents.

EXAMPLE 25

TMK1 cells, low-differentiating epithelial cells, were suspended at $0.5\times10^5$ cells/ml in RPMI 1640 culture medium containing 5–10% FCS in a 35-mm dish, followed by incubation for 2 days. EGF (10 ng/ml) and each pyrimidine compound were then added either singly or in combination to the cell culture and 5 hours or 8 hours later, the morphological form of the cells was observed. In the case of 2-piperazino-6-methyl-5-oxo-5,6-dihydro(7H)pyrro[3,4-d] pyrimidine maleate, for example, only slight morphological changes were observed from the fifth hour to day 1 when this pyrimidine derivative was singly added in an amount of 1 mM. At 10 ng/ml of EGF, however, significant morphological changes were observed as early as day 1, presenting scattering. In the culture of the cells as control, strong intercellular bonds and formation of colonies, which are characteristic of epithelial cells, were observed.

When cultured with the addition of both EGF and the compound according to the present invention, still more marked intensive morphological changes were observed compared with the addition of EGF alone. The process of the cells similar to neurites sprouted as early as 8 hours later, and extended further, thereby forming a dense network on day 1. When the test agent was removed, these morphological changes disappeared and the state of the cells returned to a colony-formed state. The compound has therefore demonstrated to induce biological activities which extremely enhance the action of EGF.

EXAMPLE 26

The shells of eggs on the 10th day after fertilization were fenestrated centrally corresponding to air spaces thereof, whereby CAMs (chorioallantoic membranes) were exposed. A nylon film in the form of a square of 3 mm in side was placed over the CAM, and onto the nylon film, a solution of bFGF as a growth and/or differentiation factor or the pyrimidine compound according to the present invention was dropped in an amount of 8 ul. Incubation was continued at 38° C. On the 72nd hour, the eggs were moved to a cool place controlled at 4° C. After the eggs were left over for 2 to 3 hours there, the degree of angiogenesis in each egg was investigated under a microscope. The angiogenesis was determined based on the number of radial blood vessels equal to or larger than 0.1 mm in diameter. Onto the nylon disk placed over the CAMS, 1, 10, and 100 ng/ml solutions of recombinant human bFGF (product of Genzyme Corporation) in physiological saline and 0.01 to 1 mM solutions of the individual pyrimidine compound in physiological saline were applied singly or in combination.

The numbers (M±SE) of new blood vessels on day 3 was 4.1±0.4 at 1 ng/ml of bFGF, 4.3±0.7 at 10 ng/ml of bFGF, and 6.1±1.1 at 100 ng/ml, respectively. In the case of 2-piperazino-6-methyl-5-oxo-5,6-dihydro(7H)pyrro[3,4-d] pyrimidine maleate, for example, the cell numbers were 3.5±0.9, 3.4±0.5 and 4.4±0.7 at 0.01 mM, 0.1 mM and 1 mM, respectively. In the control group added with physiological saline alone, the number of cells was 1.4±0.3. In contrast, in the groups in which bFGF and the compound of the present invention were both added, the number of new vessels were 8.1±1.1 in the case of bFGF+0.01 mM of the compound of the present invention, 8.5±0.8 in the case of bFGF+0.1 mM of the compound of the present invention, and 9.3±0.5 in the case of bFGF+1 mM of the compound of the present invention. It has hence been understood that the angiogenesis ability of bFGF is synergistically enhanced by the compound according to the present invention. The invention according to the present invention also has in vivo wound-healing effects, which are in conformity with those found in the in vitro experiment. This experimental method has therefore been recognized to be excellent as a screening method for wound-healing agents.

EXAMPLE 27

Platelet-derived growth factor (PDGF) has been found as a proliferation-stimulating factor for fibroblasts and arterial smooth muscle cells (SMC) from platelets, SMC, vascular endothelial cells, monocytes and transformed cells (for example, Kondo, et al., "J. Biol. Chem.", 268, 4458 ff, 1993). PDGF forms a homodimer or heterodimer of A-chains and/or B-chains and takes part in the growth and migration of cells, so that PDGF plays an important role in the healing of a wound (for example, Ross, et al., "J. Biol. Chem.", 267, 22806 ff, 1992).

When rat aortic endothelial cells are peeled off by a balloon-tip catheter, platelets adhere a damaged site of a vessel wall and thrombin, serotonin, PDGF and the like are released from their α-granules. (McNamara, et al., "J. Clin. Invest.", 91, 94 ff, 1993). Further, for SMCs around the injury, the phenotype of said SMCs having been changed from a contraction type to a synthesis type, proliferation and migration are induced by the above-described factors (Fanger, et al., "Circ. Res.", 77, 645 ff, 1993). At this time, thrombin tentatively induces transcription of PDGF-A mRNAs in SMC and reduces the expression amount of PDGF receptor mRNAs tentatively (Okazaki, et al., "Circ. Res.", 71, 1285 ff, 1992). SMCs which have been cultured in a culture flask show a synthesis phenotype and, when thrombin is added, a change similar to that observed upon injury by the balloon-tip catheter is observed on the expression of PDGF-A mRNAs and PDGF receptor mRNAs (Okazaki, et al., ibid.). In cultured rat SMCs, on the other hand, three kinds of PDGF-A transcripts of different lengths (2.9 kb, 2.3 kb, 1.7 kb) are observed. Different degrees of induction of the respective transcripts have been found between the addition of thrombin and that of serotonin (Okazaki, et al., ibid.).

With the foregoing background in view, effects of the combined use of the compound according to the present invention on the induction of expression of PDGF-A moieties, which act on a blood vessel under restoration, by thrombin or serotonin, were investigated using cultured rat SMCs.

Culture of arterial smooth muscle cells (SMCs)

SMCs were prepared following the method proposed by Ross and Klebanoff in "J. Cell. Biol.", 50, 159 ff, 1971 with partial modifications. A rat thoracic aorta was excised. After the tunica externa was peeled off, the tunica media and the tunica intima were minced into 2–3 mm$^2$. The minced sections were placed standstill in a 25-cm$^2$ flask which contained Waymouth's MB 752/1 medium containing 10% FBS and 80 ng/ml of gentamycin (product of Schering-Plough Corp.), followed by incubation at 37° C. for 2 to 3 weeks in the presence of 5% carbon dioxide gas (primary culture). The same volume of a trypsin-EDTA solution was added to the flask. After the sections were treated at 37° C. for 5 minutes to peel off cells, the cells were diluted with 10% FBS-Waymouth's MB 752/1 medium and then subcultured (second generation). Subculture was successively conducted likewise whenever the SMC became confluent. In the following experiments, the cells from the 5th generation to the 12th generation were employed.

Conditions for the addition of thrombin or serotonin

After reach in confluence of cells, the cultured SMCs were cultured for 2 days in a serum-free medium to avoid influence of serum. The SMCs were then added with thrombin (1.0 U/ml) or serotonin (5 μM), followed by incubation at 37° C. for 6 hours under which bring about induction of PDGF-A mRNAs at the maximum. To prevent dissociation of ribosomes and mRNAs, cycloheximide (100 μg/ml) was added 5 minutes before cells were collected.

Preparation of polysome fraction

Preparation of a polysome fraction and extraction of RNAs were conducted following the method proposed by Kasper, et al. in "J. Biol. Chem.", 267, 508 ff, 1992 with slight modifications. The cells, which had been collected by the treatment with trypsin, were washed with PBS containing cycloheximide (100 μg/ml). A cell precipitate was then added with 500 μl of a high-salt lysis buffer (20 mM Tris-HCl pH 7.5, 250 mM NaCl, 5 mM MgCl2, 0.1% Nonidet P-40, 0.2% DOC) for homogenization. The homogenate was centrifuged under 12,000×g at 4° C. for 10 minutes. The resulting supernatant was added with 67 μl of a heparine mix (7.4 mg/ml heparine, 1.1M NaCl, 15 mM DTT and RNasin). 200 μl of the extract were layered on 5 ml of 0.5–1.25M linear sucrose gradient (which contained 20 mM Tris-HCl pH 7.4, 10 mM NaCl, 3 mM MgCl$_2$), followed by centrifugation under 45,000 rpm for 90 minutes in a "Hitachi RP55ST". While monitoring the absorbance at 260 nm, ten (10) fractions were obtained. To prepare samples for the extraction of RNAs, the fractions were individually added with SDS and proteinase K to give final concentrations of 1% and 0.2 mg/ml, respectively. Subsequent to incubation at 37° C. for 1 hour, each fraction was extracted once with ½ volume of phenol, twice with ½ volume aliquots of chloroform, and once with the equal volume of chloroform, whereby proteins were removed. The water layer was added with glycogen (20 μg/ml) as a coprecipitant and then with 0.03M of sodium acetate, and RNAs were caused to precipitate with 2 volumes of ethanol.

Northern blot analysis

After RNAs were incubated at 65° C. for 5 minutes in a solution containing 60% of formamide, 5.9% of formaldehyde and the equal volume of MOPS buffer (10 mM MOPS pH 7.0, 4 mM NaOAc, 0.5 mM EDTA), electrophoresis was conducted across 1.2% agarose gels containing the equal volume of MOPS buffer so that RNAs were. isolated. After the gel was washed with 20 volumes of SSC, RNAs were blotted overnight to a Gene Screen Plus membrane by the capillary method. Fixing of the RNAs was conducted by exposing them for 1 minute at a distance of 10 cm from a 15-W sterilamp. Using a "QuickHyb Hybridization Solution" (product of Strategene Ltd.), hybridization was conducted following the instruction manual attached to the solution. Results of autoradiography were quantitated with reference to the NIH Image.

Effects of 2-piperazino-6-methyl-5-oxo-5,6-dihydro-(7H) pyrro[3,4-d]pyrimidine maleate on the expression and translation of PDGF-A mRNAs in rat SMCs To investigate effects of 2-piperazino-6-methyl-5-oxo-5, 6-dihydro(7H)pyrro[3,4-d]pyrimidine maleate on the expression of PDGF-A mRNAs, the compound was added to cultured rat SMCs in the presence of serotonin or thrombin to give a final concentration of 0.1 mM, and a northern blot analysis was conducted. Expression amount of 1.7 kb PDGF-A mRNAs by the sole addition of thrombin, serotonin and the invention compound were 1.5 times, 1.7 times and 1.4 times, respectively, compared with an expression amount of PDGF-A mRNAs in a serum-free culture medium as control. Combined use of the invention compound with thrombin was found to provide PDGF-A mRNAs 4.5 times as much as those available from the treatment with thrombin alone, whereas combined use of the invention compound with serotonin was recognized to provide PDGF-A mRNAs 1.6 times as much as those available from the treatment with serotonin alone. Further, the combined use of thrombin with the invention compound also provided 2.3 kb mRNAs and 2.9 kb mRNAs in greater amounts.

From the above results, the possibility has been indicated that the invention compound has a potential to promote a signal transduction mechanism induced by thrombin or serotonin, or has a potential to inhibit dissociation of PDGF-A mRNAs. Further, as a result of the addition of the invention compound, a band corresponding to hybridization of 1.3 kb PDGF-A with (-)RNA probe was additionally detected. This indicates the possibility that the invention compound may affect the splicing of PDGF-A mRNAs.

To determine effects of the invention compound on the translation of PDGF-A mRNAs, the polysome distribution of PDGF-A mRNAs was investigated. Although 1.7 kb mRNAs expressed when a serum-free culture medium was used were mostly in the non-translated form, they were converted into a translated form by the addition of the invention compound. 1.3 kb mRNAs whose expression was induced by the addition of the invention compound were also in a translated form. In the case of the cells added with thrombin alone, 1.7 kb, 2.3 kb and 2.9 kb mRNAs all included both those in a translated form and those in the non-translated form. In contrast, the cells added with both thrombin and the invention compound were converted into a translated form. In the case of the cells added with serotonin alone, the three kinds of mRNAs so induced were all in translated forms, respectively. Considering the results of the preceding item into parallel consideration, the possibility has been indicated to the effect that the invention compound may specifically promote translation of PDGF-A mRNAs, thereby increasing the stability of the PDGF-A mRNAs and increasing the amount of PDGF-A in cells.

Effects of the invention compound on the synthesis of PDGF-A by SMCs

Effects of the invention compound on the synthesis of a PDGF-A protein in SMCs were investigated by immunoprecipitation of cytoplasm fraction of cells labeled with [$^{35}$S]methionine while using an anti-human PDGF-AA antibody (product of COSMO BIO CO., LTD.). In the case of cells added with the invention compound, a band was observed around about 16 kDa from the 8th hour in both the presence and the absence of serotonin or thrombin. In the case of cells not added with the invention compound, a band was detected at 16 kDa from the 10th hour. From the above results, the invention compound has been found to promote the translation of PDGF-A mRNA.

From the above experiments, it has been indicated that the invention compound acts in a stage after the transcription of PDGF-A and accelerates the induction of PDGF-A, which serves to repair blood vessels, via thrombin or serotonin in SMCs.

EXAMPLE 28

In gastrointestinal ulcer diseases represented by gastroduodenal ulcer, the processes of occurrence and restoration of an injury such as the gastric mucosa have been studied primarily from the viewpoint of an offense factor, a defense factor or the like on the basis of an in vivo experimental model in which rats or the like were used. In an in vivo model, relevant elements are diverse and therefore an experimental system is complex, thereby making it difficult to analyze an element which relates to an individual system. An in vitro system which makes use of cultured cells allows to simplify an experimental system and to study a single element at each level. Accordingly, the activity of each invention compound was investigated based on a novel wound repair model developed by Watanabe et al. and making use of primary cultured gastric mucosal cells ("Gastroenterology", 104, A222, 1993).

Primary cultured gastric mucosal cells were prepared by mechanically peeling and mincing the gastric mucosa of a rabbit having a body weight of 2 kg and then digesting the minced gastric mucosa with 0.07% collagenase. The primary cultured gastric mucosal cells were cultured at a cell concentration of 3.3×10$^5$ cells/ml in F-12 culture medium containing 10% fetal calf serum added therein. For this cultivation, a culture dish (60 mm in diameter) coated with collagen type I was used. After full formation of a confluent cell sheet was confirmed in 48 hours after the initiation of the cultivation, a circular artificial wound of a predetermined area (about 2 mm$^2$) was mechanically made and the confluent cell sheet with the artificial wound was provided for an experiment. The process of restoration of the wound was determined by inputting single-frame images at intervals of 90 seconds through a time-lapse VTR connected to a phase microscope, continuously recording such images under conditions of 37° C. and 5% $CO_2$ and then measuring the area of the artificially wounded region at intervals of 12 hours with an image analyzer. To investigate the proliferation ability of cells, the cells were cultured while adding BrdU at intervals of 12 hours after the formation of the wound. Using an anti-BrdU antibody, the cells in the S phase were stained to identify proliferated cells. This process is expected to be determined with substantially the same results even when PNCA staining is used.

Immediately after the formation of the artificial wound, EGF (1–10 ng/ml) and 0.01–0.1 mM of 2-piperidino-7-methyl-6-oxo-5,6-dihydro(7H)pyrro[2,3-d]pyrimidine maleate (Compound A) or 0.01–0.1 mM of 2-piperazino-6-methyl-5-oxo-5,6-dihydro(7H)pyrro[3,4-d]pyrimidine maleate (Compound B) were added either independently or as a mixture to the gastric mucosal cell culture which had been rendered free of serum. Their effects on the process of restoration were measured under the above-described parameters. EGF promoted migration and proliferation of the cells in a concentration-dependent manner and accelerated the speed of restoration. Compound A and Compound B both did not show repairing effects in the absence of EGF, but further promoted the EGF-induced acceleration of cell restoration in a concentration-dependent fashion. In each of the control group and the medicament-added groups, the area of the wounded region was measured at the 0th hour, 12th hour, 24th hour, 36th hour and 48th hour. The measurement results will be given in this order.

The control group and the groups added with the medicament at the respective concentrations were each subjected to the experiment with n=5. The results will each be presented as a (mean±S. D.) mm2. A test of significance was conducted relative to the control group. * stands for p<0.05,  for p<0.01, * for p<0.001. A further test of significance was conducted relative to a group added with 10 ng/ml of EGF. + stands for p<0.05, and ++ for <0.01.

Control group:
2.07±0.06, 1.06±0.04, 0.49±0.03, 0.26±0.03, 0.
10 ng/ml EGF group:
2.06±0.06, 0.91±0.03*, 0.46±0.15, 0.08±0.04*, 0.
EGF +0.01 mM Compound A group:
2.06±0.05, 0.72±0.36, 0.39±0.04, 0.05±0.04*, 0.
EGF+0.1 mM Compound A group:
2.08±0.08, 0.80±0.04*,++, 0.24±0.05*'+, 0***'+, 0.
EGF+0.01 mM Compound B group:
2.06±0.04, 0.92±0.05, 0.38±0.05, 0.07±0.04***, 0.
EGF+0.1 mM Compound B group:
2.06±0.04, 0.83±0.05*'+, 0.29±0.07, 0*'+, 0.

From the above findings, it has been ascertained that the gastric mucosal wound repairing action of EGF can be potentiated by the addition and combined use of the compound according to the present invention. Further, similar repair-promotion-enhancing effects were also observed by combined use of another growth factor such as HGF, TGF-α, insulin or Midkine and the compound according to the present invention. The compound according to the present invention also has in vivo repairing effects for gastrointestinal ulcer. This is in conformity with the in vitro finding. The present experimental method has therefore been confirmed to be excellent as a screening method for wound-healing agents.

EXAMPLE 29

The tibia of each Wistar (body weight: 260–330 g) was broken manually and stabilized in situ by using a 22G syringe needle as an intramedullary nail under anesthesia by pentobarbital. The rats were divided into two groups. To one of the groups, 2-piperazino-6-methyl-5-oxo-5,6-dihydro (7H)pyrro[3,4-d]pyrimidine maleate was intraperitoneally administered at 5 mg/kg once a day everyday for 7 days from immediately after the fracture. The other group was used as a control group, to which physiological saline was administered likewise. The rats in both the groups were sacrificed on the 7th day. The broken tibia of each rat was decarbonized, embedded in paraffin and then subjected to HE staining. The texture of the fractured site was pathohistologically examined. In the control group, proliferation mesenchymal cells, which were considered to be derived from periosteal cells, and membranous ossification of an osteoid tissue were observed centering around the fractured site on the 7th day after the fracture. Further, honeycomb-shaped proliferation of chondrocytes in a small number associated with formation of a cartilage matrix was observed inside the mesenchymal cells. On the other hand, according to a histological finding on the 7th day after the fracture in the group administered everyday with 5 mg/kg of the invention compound, marked proliferation of mesenchymal cells which was considered to be derived from periosteal cells was observed at the fractured site of each rat. Inside the fractured site, prolifeation of chondrocytes associated with formation of a hyaline cartilage matrix enchondral ossification was observed in a quantity apparently much greater than that of the control group.

EXAMPLE 30

Action of 2-piperazino-6-methyl-5-oxo-5,6-dihydro(7H) pyrro[3,4-d]pyrimidine maleate on in vivo chondrogenesis was studied in detail by preparing a rat bone defect model which permits observation of bFGF-derived formation of a hyaline cartilage matrix. Embedment of a bFGF-containing pellet in a bone defect of the model permits easy observation of formation of a hyaline cartilage matrix under the periosteum around the bone defect. Rats were divided into three groups. The rats in one of the groups were each embedded in a formed bone defect (diameter: 2.6 mm) thereof with a hydroxyethyl methacrylate pellet (10 mg) which contained bFGF (0.5 µg). The rats in another one of the groups were each embedded likewise with a hydroxyethyl methacrylate pellet (10 mg) which contained bFGF (0.5 µg) and the invention compound (0.5 mg). The rats in the remaining group, that is, a control group were each embedded similarly with a pellet which contained physiological saline. After the rats in all the three groups were sacrificed seven days later, action of bFGF or the invention compound on the process of chondrogenesis on enchondral ossification around the bone defect was investigated. On the 7th day after the formation of the bone defect, the tibia of each rat was histologically examined around the bone defect. Although formation of only a membranous ossification was observed in the bone defect in the control group, formation of a hyaline cartilage matrix in a small amount was observed under the periosteum around the bone defect in which the bFGF-containing pellet was embedded. Further, in the group embedded with the pellet containing bFGF and the invention compound, a hyaline cartilage matrix was formed around the bone defect in an amount apparently larger than that formed in the group embedded with the bFGF-containing pellet.

From the above results, it has been indicated that the invention compound promotes and induces endochondral ossification by enhancing the action of bFGF on the tissue of a fractured site in the process of healing of the fracture.

EXAMPLE 31

Formation of collagen has been found to have important significance in the process of healing of a skin or muscle cut in a skin/muscle cut-suture rat model. As a feature specific to this model, collagen fibers form a plate-like structure so that they cross at right angles with muscle fibers, and macrophages accumulate on the plate-like structure. This plate-like collagen is considered to serve in such a way that it prevents detachment or fraying of both cut ends of muscle fibers and assists formation of an anastomosis. An observation under a scanning electron microscope has also obtained a finding indicative of the possibility that 2-piperazino-6-methyl-5-oxo-5,6-dihydro(7H)pyrro-[3,4-d]pyrimidine maleate effectively acts for the promotion of the formation of such plate-like collagen and the accumulation of macrophages.

EXAMPLE 32

As fulminant hepatitis may develop hepatocellular regeneration failure despite a high HGF concentration in blood, use of a medicament capable of enhancing effects of a growth factor is desired. Activities of a compound according to the present invention as a hepatic medicine were investigated using primary cultured cells and Ito (star) cells of rat.

An SD male rat of about 200 g in body weight was sacrificed by perfusion of collagenase-containing physiological saline. Hepatocytes were immediately collected and then spread at $5.0 \times 10^4$ cells/cm$^2$ over plates, followed by the initiation of cultivation. Two hours later, the culture medium was replaced by a fresh supply of the culture medium. Twenty-four hours later, EGF and [$^3$H]-leucine (1 µCi/ml) were added to half the number of the plates with or without addition of 2-piperidino-7-methyl-6-oxo-5,6-dihydro(7H) pyrro[2,3-d]pyrimidine maleate, respectively. At the same time, EGF was added to the remaining plates with or without addition of the invention compound, respectively. Forty-six hours later, the latter plates were both added further with [$^3$H]-tymidine (2 µCi/ml). Forty-eight hours later, each culture was filtered under suction to harvest the cells so cultivated. Trichloroacetic acid (TCA) was added to the thus-harvested cells to obtain a TCA precipitate. The TCA precipitate was formed into a pellet. The pellets which had been obtained from the [$^3$H]-tymidine-added cultures, respectively, were each dissolved with 0.1N NaOH. The resulting solution was added to a liquid scintillator and the amount of DNA synthesized by the cells was measured by a liquid scintillation counter. Likewise, the pellets which had been obtained from the [$^3$H]-leucine-added cultures, respectively, were each boiled at 70° C. to extract soluble matter. The extract so obtained was also added with TCA to obtain a TCA precipitate. The TCA precipitate was dissolved with 0.1N NaOH. The resulting solution was added to the liquid scintillator and the amount of proteins synthesized by the cells was measured by the liquid scintillation counter.

On the other hand, an SD male rat of about 300 g in body weight was sacrificed by perfusion of physiological saline containing collagenase and proteinase. Ito (star) cells were collected and then spread at $1.25 \times 10^5$ cells/cm$^2$ over plates, followed by the initiation of cultivation. The cultivation was conducted for 6 days. In a manner similar to the procedures described above, some of the plates were added with the invention compound and [$^3$H]-leucine 24 hours before harvest, while the remaining plates were added with the invention compound 24 hours before harvest and were then added with [$^3$H]-tymidine two hours before the harvest. The synthesized amount of DNA and that of proteins were measured. Further, after Ito cells were cultured for 6 days, the invention compound and b-FGF were added. Subsequent to cultivation for 30 minutes, 0.1M of ascorbic acid and 0.5 mM of β-aminopropionitrile fumarate were added, followed by cultivation for 1 hour. [2,3-$^3$H]-proline (10 μCi/ml) was added, followed by further cultivation for 24 hours. The culture was separated into the culture medium and the resultant cells, and a TCA precipitate was formed. After the precipitate was dissolved with 0.1N NaOH, the cells were incubated in the presence of bacterial collagenase. The reaction was terminated with TCA-tannic acid, followed by the formation of a pellet. A supernatant fraction was added to the liquid scintillator and the amount of proteins synthesized by the cells was measured by the liquid scintillation counter.

When EGF was added in the above test, the synthesis of DNA by the hepatocytes significantly increased in the presence of 10 μM of the invention compound. At that time, no change was observed in the expression of mRNA and the concentration of albumin in the supernatant of the culture. Without addition of EGF, the invention compound was not recognized to promote the synthesis of DNA. The synthesis of DNA and collagen by the star cells was lowered depending on the amount of the invention compound in a range of from 1 μM to 100 μM irrespective of the presence or absence of b-FGF. In the absence of b-FGF, the expression of α$_2$-smooth muscle actin (αSM) was lowered by the addition of the invention compound. On the other hand, the expression of αSM was lowered by the presence of b-FGF but was allowed to recover by the addition of the invention compound in a quantity-dependent manner.

As is readily understood from the foregoing, the invention compound acts as a comitogen for hepatocytes but does not change the synthesis of albumin. Further, the invention compound suppressed the proliferation of star cells and also the synthesis of collagen. b-FGF has also been found to suppress the expression of αSM by star cells. It has therefore been suggested that the invention compound may be useful as a therapeutic for suppressing hepatitis-induced fibrosis and promoting proliferation of hepatocytes.

EXAMPLE 33

The procedures of Example 4 were followed except for the additional inclusion of Midkine in an amount of 1 mg per vial.

EXAMPLE 34

The procedures of Example 5 were followed except for the additional inclusion of Midkine in an amount of 1 mg per ampoule.

EXAMPLE 35

The procedures of Example 6 were followed except for the additional inclusion of Midkine in an amount of 0.2 mg per unit preparation.

EXAMPLE 36

The procedures of Example 7 were followed except for the additional inclusion of Midkine in an amount of 0.2 mg per unit preparation.

Experiment 1

Some of the compounds which are useful in the practice of the present invention were orally administered to 5-weeks old male ddy mice and 8-weeks old male Wistar rats. Their toxicity was determined 24 hours later. For the mice, those compounds were found to have an LD50 value larger than 1,000 mg/kg, or in a range of from 550 mg/kg to 1,000 mg/kg. For the rats, on the other hand, they were found to have an LD50 value larger than 1,700 mg/kg, or in a range of from 550 mg/kg to 1,000 mg/kg. Accordingly, the compounds useful in the practice of the present invention can be regarded as medicaments having low toxicity and high safety in general. For the specific values of their LD50 values, reference may be made to the specifications of certain patent applications which were filed in the name of the present inventors and have already been laid open to the public or even registered.

What we claim are:

1. A method for healing compromised tissues, comprising administering a tissue-healing agent comprising a pyrimidine derivative of formula (1) or (2), or a pharmaceutically acceptable salt thereof, to a patient having compromised tissues where a growth/differentiation factor, a growth hormone or a cytokine is produced and/or present, in an amount efficient to potentiate or modify biological activities of the growth/differentiation factor, the growth hormone or the cytokine, said compromised tissues being selected from the group consisting of simple incised wounds or cuts, burns, scalds, bone fractures, tooth extraction wounds, operative wounds during surgical operations in cornea and organs, body epithelial or endothelial ulcers, keloid, texture injuries of gastrointestinal mucosae, hepatic injuries, bone damages, pseudoarthroses, necrosis of femoral head, ligamentous damages, periodontal damages, vascular damages, myocardial infarctions, arterial scleroses, post-PTCA re-perfusion disorders, injuries by drugs or radiations, hemorrhoids, apellous wounds, skin cuts, artery iland skin flaps, digestive tract ulcers, intra-aortic balloon catheter paratripsises, and cornea injuries:

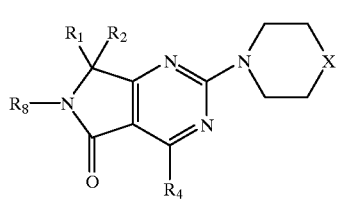

(1)

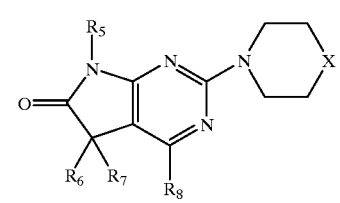

(2)

wherein $R_1$ to $R_8$ independently represent a hydrogen atom, a lower alkyl group, $CH_3OCH_2CH_2$-, $CH_2CONH_2$, -$COCH_3$, -$COC_2H_5$ or -$CH_2OCOC_2H_5$, and X represents =NH, =N—$CH_3$, =N—$C_2H_5$, =N-ph, =N—$CH_2$-ph, =N—$CH$-$ph_2$, =N—$COCH_3$, =N—$COOC_2H_5$, =N—SO$_2$CH$_3$, =CH$_2$, =CHCH$_3$, =CHC$_2$H$_5$, -O- or -S- in which ph stands for a phenyl group, in an amount sufficient to facilitate healing said compromised tissues.

2. A method according to claim 1, wherein said pyrimidine derivative is 2-piperazino-6-methyl-5-oxo-5,6-dihydro(7H)pyrro[3,4-d]pyrimidine or a pharmaceutically acceptable salt thereof.

3. A method according to claim 1, wherein said pyrimidine derivative is 2-piperidino-7-methyl-6-oxo-5,6-dihydro(7H)pyrro[2,3-d]pyrimidine or a pharmaceutically acceptable salt thereof.

4. A method according to claim 1, wherein said pyrimidine derivative is 2-(4-ethyl-piperidino)-7-methyl-6-oxo-5,6-dihydro(7H)pyrro[2,3-d]pyrimidine or a pharmaceutically acceptable salt thereof.

5. A method according to claim 1, wherein said pyrimidine derivative is 2-piperidino-5,5,7-trimethyl-6-oxo-5,6-dihydro(7H)pyrro[2,3-d]pyrimidine or a pharmaceutically acceptable salt thereof.

6. A method according to claim 1, further comprising administering to said patient an additional substance comprised of a growth or differentiation factor, a growth hormone or a cytokine.

7. A method according to claim 3, wherein said biological activities are activities of at least one biological substance selected from the group consisting of an epidermal growth factor (EGF), an acidic fibroblast growth factor (aFGF), a basic fibroblast growth factor (bFGF), an α or β transforming growth factor (TGF), a vascular endothelial cell growth factor (VEGF), a platelet-derived growth factor (PDGF), a platelet-derived endothelial cell growth factor (PDECGF), a bone morphogenic protein (BMP), a hepatocyte growth factor (HGF), midkine, a tumor necrosis factor (TNF), insulin, an insulin-like growth factor (IGF-I, II), a keratinocyte growth factor, an endothelial cell growth factor (ECGF), a fibroblast-derived epithelial cell growth factor, a granulocyte-colony stimulating factor (G-CSF), a macrophage-colony stimulating factor (M-CSF), a granulocyte-macrophage-colonystimulating factor (GM-CSF), thrombopoietin (TPO), a leukemia inhibitory factor (LIF), a stem cell factor (SCF), erythropoietin (EPO), an adult T cell leukemia-derived factor (ADF), macrophage inflammatory protein 1α(MIP-1α), transferrin, thrombin, thrombomodulin, interleukin-1 (IL-1), interleukin- (IL4), interleukin-6 (IL-6), interleukin-8 (IL-8), a heparin releasing factor (HRF), a monocyte chemotactic activator, a calcitonin gene related peptide (CGRP), superoxide dismutase (SOD), an angiotensin, a prostaglandin, serotonin, collagen, fibronectin, laminin and a homologue of any of the foregoing.

8. A method according to claim 1, further comprising administering to said patient an EGF.

9. A method according to claim 1, further comprising administering to said patient a bFGF.

10. A method according to claim 1, further comprising administering to said patient a Midkine.

11. A method according to claim 2, wherein said pyrimidine derivative is in the form of a maleate salt.

12. A method according to claim 3, wherein said pyrimidine derivative is in the form of a maleate salt.

13. A method according to claim 4, wherein said pyrimidine derivative is in the form of a maleate salt.

14. A method according to claim 5, wherein said pyrimidine derivative is in the form of a maleate salt.

15. A method according to claim 6, wherein said additional substance is selected from the group consisting of an epidermal growth factor (EGF), an acidic fibroblast growth factor (aFGF), a basic fibroblast growth factor (bFGF), a further FGF, an α or β transforming growth factor (TGF), a vascular endothelial cell growth factor (VEGF), a platelet-derived growth factor (PDGF), a platelet-derived endothelial cell growth factor (PDECGF), a bone morphogenic protein (BMP), a hepatocyte growth factor (HGF), Midkine, a tumor necrosis factor (TNF), insulin, an insulin-like growth factor (IGF-I, II or the like), a keratinocyte growth factor, an endothelial cell growth factor (ECGF), a fibroblast-derived epithelial cell growth factor, G-CSF, M-CSF, GM-CSF, TPO, LIF, SCF, EPO, ADF, MIP-1α, transferrin, thrombin, thrombomodulin, interleukin-1 (IL-1), interleukin-4 (IL-4), interleukin-6 (IL-6), interleukin-8 (IL-8), a heparin releasing factor (HRF), a monocyte chemotactic activator, a calcitonin gene related peptide (CGRP), SOD, an angiotensin, a prostaglandin, serotonin, collagen, fibronectin, or laminin.

* * * * *